United States Patent
Takami et al.

(10) Patent No.: US 9,974,596 B2
(45) Date of Patent: May 22, 2018

(54) HIGH-FREQUENCY CONTROL UNIT AND HIGH-FREQUENCY TREATMENT SYSTEM

(71) Applicant: OLYMPUS CORPORATION, Hachioji-shi, Tokyo (JP)

(72) Inventors: Sadayoshi Takami, Hachioji (JP); Tsuyoshi Hayashida, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/263,658

(22) Filed: Sep. 13, 2016

(65) Prior Publication Data

US 2016/0374746 A1 Dec. 29, 2016

Related U.S. Application Data

(63) Continuation of application No. PCT/JP2015/081759, filed on Nov. 11, 2015.

(30) Foreign Application Priority Data

Nov. 14, 2014 (JP) ................................. 2014-231203

(51) Int. Cl.
*A61B 18/00* (2006.01)
*A61B 18/12* (2006.01)

(52) U.S. Cl.
CPC .............. *A61B 18/1206* (2013.01); *A61B 2018/00672* (2013.01); *A61B 2018/00678* (2013.01);
(Continued)

(58) Field of Classification Search
None
See application file for complete search history.

(56) References Cited

U.S. PATENT DOCUMENTS 6,183,468 B1 * 2/2001 Swanson ............ A61B 18/1206
606/34
8,512,332 B2 * 8/2013 Collins .............. A61B 18/1206
606/38
(Continued)

FOREIGN PATENT DOCUMENTS

JP 2008-114042 A 5/2008
JP 2009-082707 A 4/2009
(Continued)

OTHER PUBLICATIONS

May 26, 2017 International Preliminary Report on Patentability issued in PCT/JP2015/081759.
(Continued)

*Primary Examiner* — Ronald Hupczey, Jr.
(74) *Attorney, Agent, or Firm* — Oliff PLC

(57) ABSTRACT

A high-frequency control unit includes an integration value calculator calculating a measured integration value, which is a measured value of an integration value of an output high-frequency electric power from an output start time, with a passage of time. The high-frequency control unit includes a target locus setting section setting target locus which indicates, with a passage of time, a target integration value that is a target value of the integration value of the output high-frequency electric power from the output start time, and a controller comparing, with a passage of time, the measured integration value with the target locus, and controlling, with a passage of time, an output state of the high-frequency electric power based on a comparison result.

6 Claims, 8 Drawing Sheets

(52) U.S. Cl.
CPC .............. *A61B 2018/00702* (2013.01); *A61B 2018/00767* (2013.01); *A61B 2018/00779* (2013.01); *A61B 2018/00827* (2013.01); *A61B 2018/00875* (2013.01); *A61B 2018/00886* (2013.01); *A61B 2018/00892* (2013.01)

(56) References Cited

U.S. PATENT DOCUMENTS

| | | |
|---|---|---|
| 2008/0015564 A1* | 1/2008 | Wham .............. A61B 18/1206 606/34 |
| 2008/0114351 A1 | 5/2008 | Irisawa et al. |
| 2009/0082765 A1 | 3/2009 | Collins et al. |
| 2010/0042101 A1 | 2/2010 | Inagaki et al. |
| 2013/0338665 A1 | 12/2013 | Tanaka et al. |
| 2014/0025064 A1 | 1/2014 | Collins et al. |

FOREIGN PATENT DOCUMENTS

| | | |
|---|---|---|
| JP | 2010-042249 A | 2/2010 |
| WO | 2013/088892 A1 | 6/2013 |

OTHER PUBLICATIONS

Feb. 9, 2016 Search Report issued in International Patent Application No. PCT/JP2015/081759.

\* cited by examiner

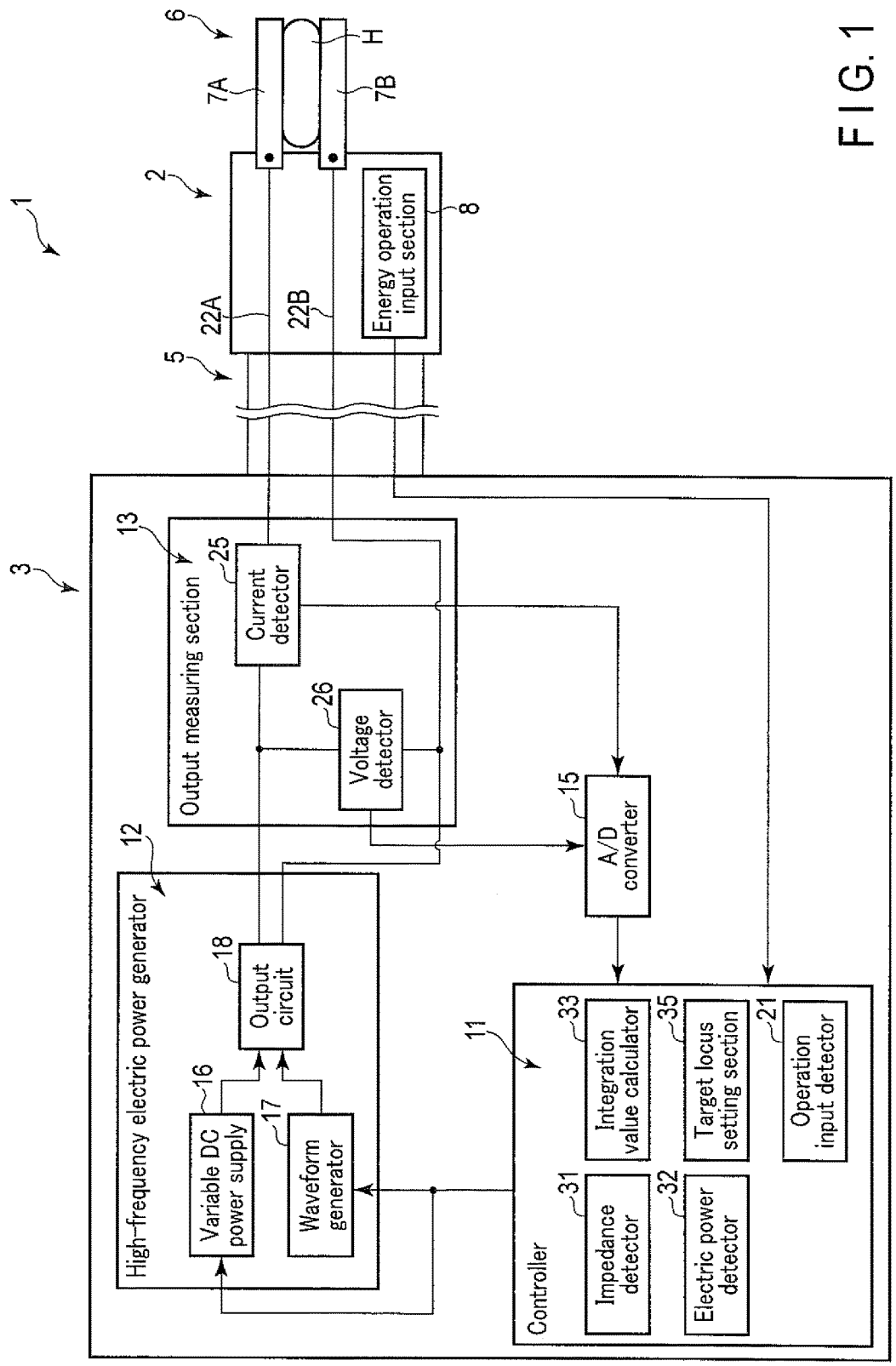
F I G. 1

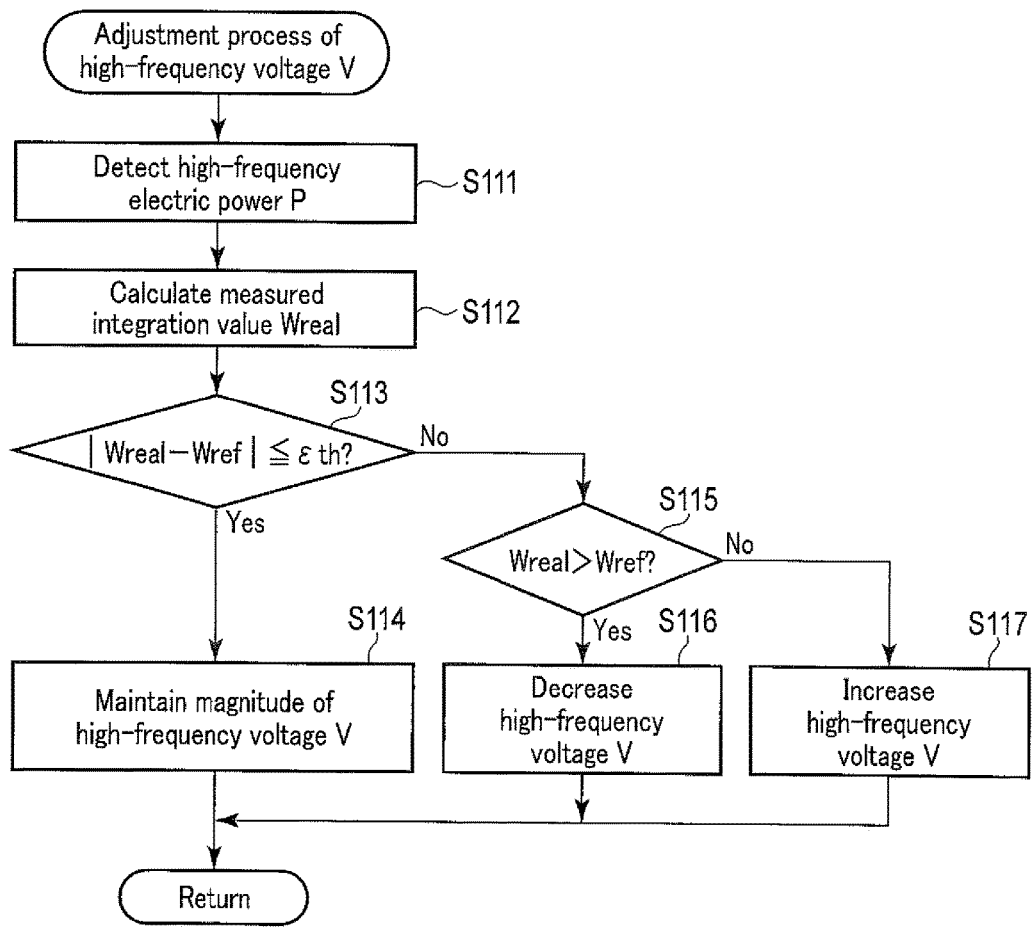
F I G. 3

HIGH-FREQUENCY CONTROL UNIT AND HIGH-FREQUENCY TREATMENT SYSTEM

CROSS-REFERENCE TO RELATED APPLICATIONS

This is a Continuation application of PCT Application No. PCT/JP2015/081759, filed Nov. 11, 2015 and based upon and claiming the benefit of priority from prior Japanese Patent Application No. 2014-231203, filed Nov. 14, 2014, the entire contents of which are incorporated herein by reference.

BACKGROUND OF THE INVENTION

1. Field of the Invention

The present invention relates to a high-frequency control unit which controls an output of high-frequency electric power that is supplied to a treatment section, and relates to a high-frequency treatment system including the high-frequency control unit.

2. Description of the Related Art

Jpn. Pat. Appln. KOKAI Publication No. 2008-114042 discloses a high-frequency treatment system which treats a treated target by supplying high-frequency electric power to two electrode portions provided in a treatment section, and causing a high-frequency current to flow to the treated target, such as a living body tissue, which is clamped between the electrode portions. In this high-frequency treatment system, there is provided a high-frequency energy generator (high-frequency electric power generator) which generates high-frequency electric power that is supplied to the treatment section. In addition, the high-frequency electric power, which is output from the high-frequency energy generator, is detected by an electric power amount detector with the passage of time. Based on a detection result by the electric power amount detector, a controller calculates, with the passage of time, an integration value (measured integration value) of the output high-frequency electric power from the output start time. At a time point when the calculated integration value has exceeded a threshold, the controller stops the output of the high-frequency electric power from the high-frequency energy generator.

BRIEF SUMMARY OF THE INVENTION

According to one aspect of the invention, a high-frequency control unit for use in a high-frequency treatment system, including: a high-frequency electric power generator configured to generate high-frequency electric power which is supplied to a treatment section; an electric power detector configured to detect, with a passage of time, the high-frequency electric power which is output from the high-frequency electric power generator; an integration value calculator configured to calculate, based on a detection result by the electric power detector, a measured integration value with a passage of time, the measured integration value being a measured value of an integration value of the output high-frequency electric power from an output start time; a target locus setting section configured to set a target locus which indicates, with a passage of time, a target integration value that is a target value of the integration value of the output high-frequency electric power from the output start time; and a controller configured to compare, with a passage of time, the measured integration value, which is calculated by the integration value calculator, with the target locus set by the target locus setting section, and configured to control, with a passage of time, an output state of the high-frequency electric power from the high-frequency electric power generator based on a comparison result.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view illustrating a high-frequency treatment system according to a first embodiment;

FIG. 3 is a flowchart illustrating a process of adjusting a high-frequency voltage, which is executed by a controller according to the first embodiment;

DETAILED DESCRIPTION OF THE INVENTION

First Embodiment

Figure 2:
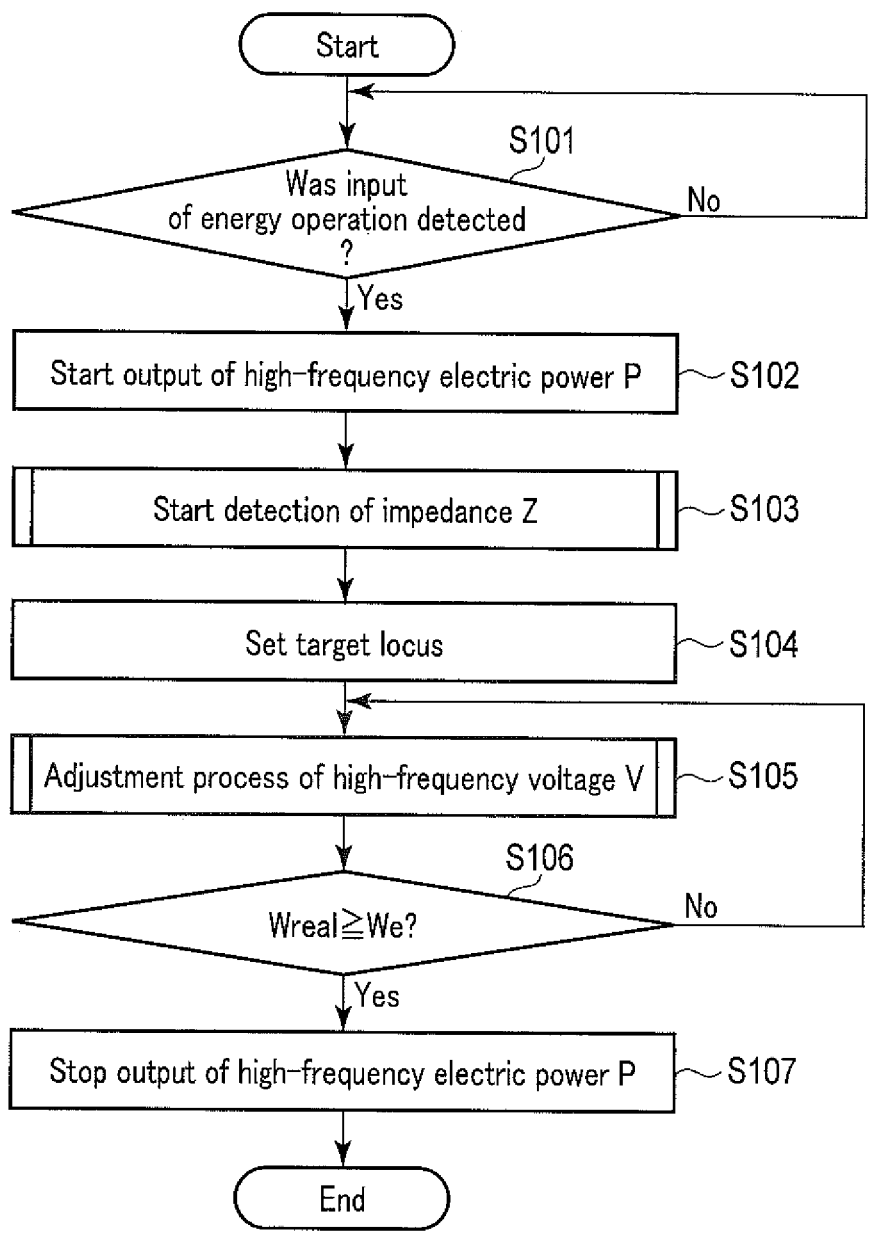
FIG. 2 is a flowchart illustrating a process in treatment by a high-frequency control unit according to the first embodiment.

A first embodiment of the present invention will be described with reference to FIG. 1 to FIG. 5. FIG. 1 is a view illustrating a high-frequency treatment system 1 according to the present embodiment. As illustrated in FIG. 1, the high-frequency treatment system 1 includes a high-frequency treatment instrument 2, and a high-frequency control unit 3 such as a high-frequency energy source device. The high-frequency treatment instrument 2 and high-frequency control unit 3 are connected via a cable 5. The high-frequency treatment instrument 2 includes a treatment section (end effector) 6 which is supplied with high-frequency electric power (high-frequency electric energy) P, and treats a treated target H, such as a living body tissue, by using the supplied high-frequency electric power P. The treatment section 6 is provided with a first electrode portion 7A and a second electrode portion 7B. In addition, the high-frequency treatment instrument 2 is provided with an energy operation input section 8, such as an energy operation button, to which an energy operation for supplying the high-frequency electric power P to the treatment section 6 is input. Incidentally, a footswitch, for instance, may be provided as the energy operation input section (8), separately from the high-frequency treatment instrument 2.

The high-frequency control unit 3 includes a controller 11, a high-frequency electric power generator 12, an output measuring section 13, and an A/D converter 15. The controller 11 is composed of a processor including a CPU (Central Processing Unit) or an ASIC (application specific integrated circuit), and a storage section such as a memory, and controls the entirety of the high-frequency control unit 3. The high-frequency electric power generator 12 includes a variable DC power supply 16, a waveform generator 17 such as a waveform generating circuit, and an output circuit 18 including an amplifier circuit. In addition, the controller 11 includes an operation input detector 21 configured to detect an input of an energy operation. The operation input detector 21 is composed of an electronic circuit (detection circuit) which is provided in, for example, a CPU or ASIC. The high-frequency treatment instrument 2 is provided with, for example, a switch (not shown) the ON/OFF state of which is changed by an energy operation being input to the energy operation input section 8. An operation signal is transmitted to the operation input detector 21 in accordance with the change of the ON/OFF state of the switch, and thereby the input of the energy operation is detected.

Based on the input of the energy operation and a set condition, the controller 11 controls the variable DC power supply 16 and the waveform generator 17. By the energy operation being input, DC power is output from the variable DC power supply 16 and a waveform (e.g. a rectangular wave) is output from the waveform generator 17 by the control of the controller 11. In addition, by the DC power and waveform being transmitted to the output circuit 18, the output circuit 18 is driven and high-frequency electric power (high-frequency electric energy) P is generated.

The output circuit 18 is electrically connected to the first electrode portion 7A via a first electric path 22A, and is electrically connected to the second electrode portion 7B via a second electric path 223. The first electric path 22A and second electric path 22B extend from the high-frequency control unit 3 through the inside of the cable 5 and the high-frequency treatment instrument 2. The generated high-frequency electric power P is output from the output circuit 18, and is supplied to the first electrode portion 7A and second electrode portion 7B of the treatment section 6 through the first electric path 22A and second electric path 22B. By the high-frequency electric power P being supplied, the first electrode portion 7A and second electrode portion 7B have mutually different electric potentials, and a high-frequency voltage V is applied between the first electrode portion 7A and second electrode portion 7B. Thereby, with the treated target H being clamped between the first electrode portion 7A and second electrode portion 7B, a high-frequency current I flows in the treated target H. Thereby, treatment using the high-frequency electric power P is performed in the treatment section 6.

In addition, the output measuring section 13 includes a current detector 25 which is a detection circuit or an ammeter, and a voltage detector 26 which is a detection circuit or a voltmeter. The current detector 25 detects, with the passage of time, the current value of the high-frequency current I which flows through a circuit including the first electric path 22A, treated target H and second electric path 22B by the output of the high-frequency electric power P. In addition, the voltage detector 26 detects, with the passage of time, the voltage value of the high-frequency voltage V applied between the first electrode portion 7A and second electrode portion 7B by the output of the high-frequency electric power P (i.e. the potential difference occurring between the first electric path 22A and second electric path 22B). Detection signals, which are indicative of a detection result by the current detector 25 and a detection result by the voltage detector 26, are converted from analog signals to digital signals by the A/D converter 15 which is composed of an analog-to-digital converting circuit or the like, and the digital signals are transmitted to the controller 11 via an interface such as a bus.

The controller 11 includes an impedance detector 31, an electric power detector 32, an integration value calculator 33, and a target locus setting section 35. The impedance detector 31, electric power detector 32, integration value calculator 33 and target locus setting section (reference locus setting section) 35 are composed of electronic circuits (a detection circuit, an arithmetic circuit, etc.) which form a CPU or ASIC. The electric power detector (electric power acquisition section) 32 detects (acquires), with the passage of time, the high-frequency electric power P which is output from the high-frequency electric power generator 12 (output circuit 18), based on the results by the current detector 25 and voltage detector 26. The high-frequency electric power P is a product between the high-frequency current I and high-frequency voltage V. Based on a detection result by the electric power detector 32, the integration value calculator 33 calculates, with the passage of time, a measured integration value Wreal which is a measured value of an integration value W of the output high-frequency electric power P from the output start time. In the meantime, the integration value W of the high-frequency electric power P is a value obtained by time-integrating the high-frequency electric power P.

The impedance detector (impedance acquisition section) 31 detects (acquires), with the passage of time, an impedance (high-frequency impedance) Z of the circuit in which the high-frequency current I flows, on the basis of the detection results by the current detector 25 and voltage detector 26. The impedance Z is a value obtained by dividing the high-frequency voltage V by the high-frequency current I. In addition, based on a detection result by the impedance detector 31, the target locus setting section 35 sets a target locus (reference locus) which indicates, with the passage of time, a target integration value (reference integration value) Wref which is a target value (reference value) of the integration value W of the high-frequency electric power P from the output start time. The controller 11 compares, with the passage of time, the measured integration value Wreal, which is calculated by the integration value calculator 33, with the set target locus. Then, based on a comparison result, the controller 11 controls the variable DC power supply 16 and waveform generator 17 via an interface such as a bus, and controls, with the passage of time, the output state of the high-frequency electric power P from the high-frequency electric power generator 12.

Next, the functions and advantageous effects of the high-frequency control unit 3 and high-frequency treatment system 1 will be described. In treatment, the treatment section 6 is inserted into the body, and the treated target H, such as a blood vessel, is gripped between the first electrode portion 7A and second electrode portion 7B. In this state, a surgeon inputs an energy operation by the energy operation input section 8.

FIG. 2 is a flowchart illustrating a process in the high-frequency control unit 3 in the treatment. In the treatment, when the operation input detector 21 detects an input of an energy operation in the energy operation input section 8 (step S101—Yes), the controller 11 controls the variable DC power supply 16 and waveform generator 17 of the high-frequency electric power generator 12, and the high-frequency electric power generator 12 (output circuit 18) starts an output of high-frequency electric power (high-frequency electric energy) P (step S102). Thereby, the high-frequency electric power P is supplied to the first electrode portion 7A and second electrode portion 72, and treatment is performed for coagulating (sealing) the treated target H by using the high-frequency electric power P.

When the high-frequency power P is output, the current detector 25 detects a high-frequency current I with the passage of time, and the voltage detector 26 detects a high-frequency voltage V with the passage of time. Then, based on detection results by the current detector 25 and voltage detector 26, the impedance detector 31 starts time-based detection of an impedance Z of a circuit in which the high-frequency current I flows (i.e. an impedance of the treated target H) (step S103). Then, based on a detection result by the impedance detector 31, the target locus setting section 35 sets a target locus (reference locus) which indicates, with the passage of time, a target integration value (reference integration value) Wref that is a target value (reference value) of an integration value W of the high-frequency electric power P from the output start time Ts (step S104). If the target locus is set, the controller 11 executes a process of adjusting the high-frequency voltage V, based on the target locus (step S105).

Figure 4:
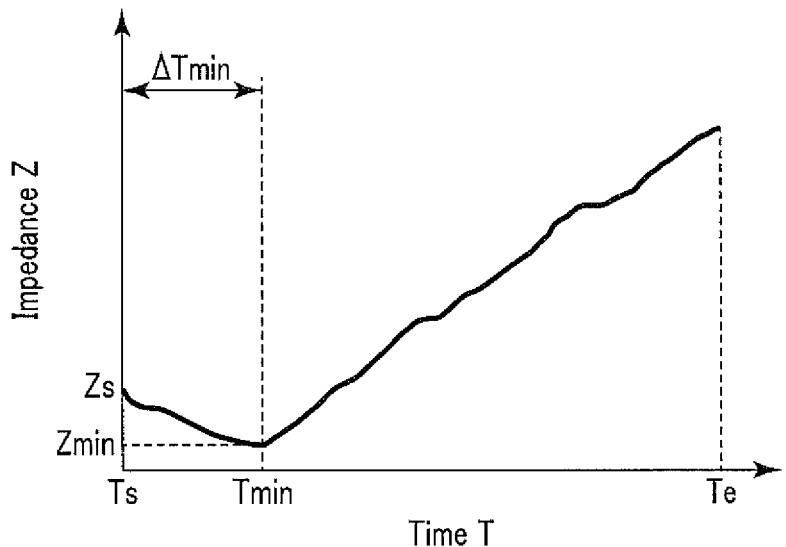
FIG. 4 is a schematic view illustrating an example of a time-based variation of an impedance in treatment using the high-frequency control unit according to the first embodiment.
Figure 5:
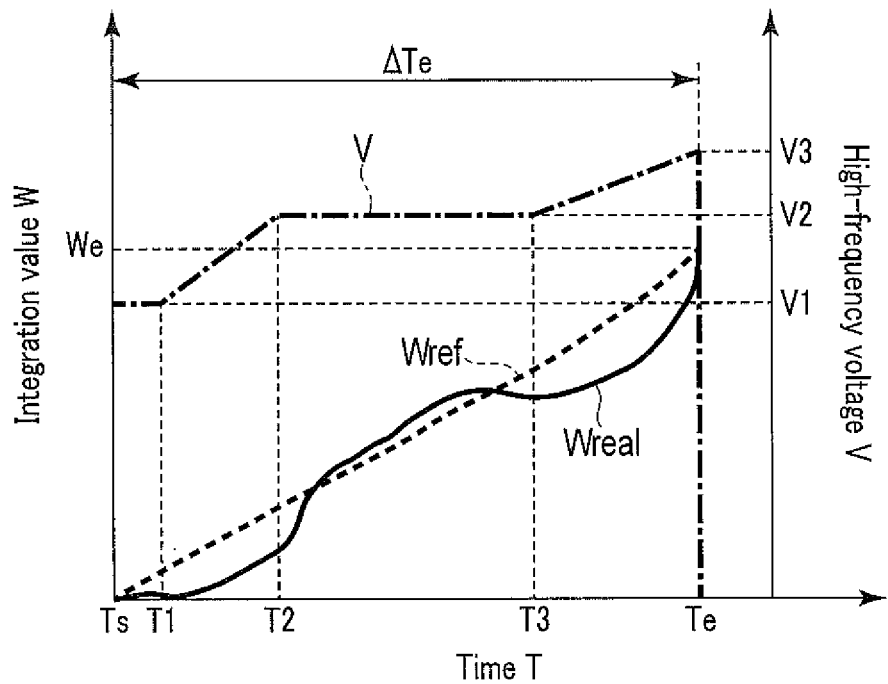
FIG. 5 is a schematic view illustrating an example of time-based variations of a target integration value of high-frequency electric power, a measured integration value of the high-frequency electric power, and a high-frequency voltage in treatment using the high-frequency control unit according to the first embodiment.

FIG. 3 is a flowchart illustrating the process (step S105 of FIG. 2) of adjusting the high-frequency voltage V (high-frequency electric power P), which is executed by the controller 11. FIG. 4 is a graph illustrating an example of a time-based variation of the impedance Z in the treatment using the high-frequency control unit 3. FIG. 5 is a graph illustrating an example of time-based variations of the target integration value Wref of high-frequency electric power P, a measured integration value Wreal of the high-frequency electric power P, and the high-frequency voltage V (output level) in the treatment. In FIG. 4, the abscissa indicates time. T, and the ordinate indicates the impedance Z. In addition, in FIG. 5, the abscissa indicates time T, and the ordinate indicates the integration value W of high-frequency electric power P, and the high-frequency voltage V. Further, in FIG. 5, the time-based variation of the measured integration value Wreal is indicated by a solid line, the time-based variation of the target integration value Wref is indicated by a broken line, and the time-based variation of the high-frequency voltage V is indicated by a dash-and-dot line.

An accretion adheres on the outer surface of the treated target H such as a blood vessel. Thus, the accretion on the treated target H is eliminated until a certain length of time has passed since an output start time Ts at which the output of high-frequency electric power P is started, and a certain length of time from the output start time Ts is needed until the treatment section 6 (first electrode portion 7A and second electrode portion 7B) comes in contact with the outer surface of the treated target H. As illustrated in FIG. 4, the impedance (high-frequency impedance) Z decreases with time, until the treatment section 6 comes in contact with the outer surface of the treated target H (i.e. while the adhesive material on the treated target H is being eliminated). Then, after the treatment section 6 came in contact with the outer surface of the treated target H (i.e. while the treated target H is being coagulated and sealed), the impedance Z increases with time. Thus, the impedance Z reaches a minimum value (local minimum value) Zmin, at a time point when the treatment section 6 has come in contact with the outer surface of the treated target H, or at a time in the neighborhood of this time point of contact. In FIG. 4, at time Tmin, the impedance Z reaches the minimum value Zmin. A time ΔTmin is needed from the output start time Ts to the impedance minimum time Tmin. In the meantime, a time point, at which a gradual decrease of the impedance Z changes to a gradual increase of the impedance Z, is detected as the impedance minimum time Tmin at which the impedance Z becomes minimum.

In step S104 of FIG. 2, the target locus setting section 35 sets a target stop integration value (reference stop integration value) We which is a target integration value Wref at a time point at which the output of the high-frequency electric power P is stopped, and a target stop time (reference stop time) ΔTe from the output start time Ts until the target integration value Wref reaching the target stop integration value We (i.e. a target time from the output start time Ts to the stop of the output). Then, based on the set target stop integration value We and target stop time ΔTe, the target locus setting section 35 sets a target locus which indicates, with the passage of time, the target integration value Wref of the high-frequency electric power P. The target stop integration value We and target stop time ΔTe are set based on the detection result by the impedance detector 31. For example, the target locus setting section 35 sets the target stop integration value We and target stop time ΔTe, based on at least one of a value Zs of the impedance Z at the output start time Ts of high-frequency electric power P, an inclination (decrease rate) σ of the variation of the impedance Z from the output start time Is until the impedance Z reaching the minimum value Zmin, and the time ΔTmin from the output start time Ts until the impedance Z reaching the minimum value Zmin. In the meantime, in the storage section (not shown) provided in the controller 11, a plurality of target loci of mutually different time-based variation patterns of the target integration value Wref are stored, and a target locus of one of the plural variation patterns is selected in accordance with a detection result of the impedance Z. In addition, the inclination σ of the variation of the impedance Z from the output start time Ts to the impedance minimum time Train is calculated by using the following equation (1).

$$\sigma = \frac{Zmin - Zs}{Tmin - Ts} = \frac{Zmin - Zs}{\Delta Tmin} \tag{1}$$

As illustrated in FIG. 3, when the process (step S105) of adjusting the high-frequency voltage V is started, the electric power detector 32 detects, with the passage of time, the high-frequency electric power P which is output from the high-frequency electric power generator 12, based on the detection results by the current detector 25 and voltage detector 26 (step S111). Then, based on a detection result by the electric power detector 32, the integration value calculator 33 calculates, with the passage of time, the measured integration value Wreal which is a measured value of the integration value W of the output high-frequency electric power P from the output start time Ts (step S112). Then, the controller 11 compares, with the passage of time, the calculated measured integration value Wreal with the target locus (target integration value Wref). Then, based on the comparison result, the controller 11 controls, with the passage of time, the output state of the high-frequency electric power P from the high-frequency electric power generator 12. In the present embodiment, the controller 11 controls the output state of the high-frequency electric power P by controlling the high-frequency voltage V.

In the time-based comparison of the measured integration value Wreal with the target locus, the controller 11 determines whether an absolute value of the difference between the measured integration value Wreal and the target integration value Wref is a predetermined threshold $\epsilon th$ or less (step S113). Specifically, it is determined whether the equation (2) is established or not.

$$|Wreal - Wref| \le \epsilon th \quad (2)$$

Thereby, the degree of a deviation of the measured integration value Wreal from the target locus is determined. When the absolute value of the difference between the measured integration value Wreal and target integration value Wref is the predetermined threshold $\epsilon th$ or less (i.e. if equation (2) is established) (step S113—Yes), the controller 11 controls the variable DC power supply 16 and waveform generator 17, thereby maintaining the magnitude of the high-frequency voltage V which is applied by the output of the high-frequency electric power P (step S114). Thereby, when the impedance Z does not vary, the magnitude of the high-frequency current 1 is also maintained, and the magnitude (output level) of the high-frequency electric power P, which is output from the high-frequency electric power generator 12, is also maintained. On the other hand, when the absolute value of the difference between the measured integration value Wreal and target integration value Wref is greater than the predetermined threshold $\epsilon th$ (step S113—No), it is determined whether the measured integration value Wreal is greater than the target integration value Wref (step S115). Specifically, it is determined whether equation (3) is established or not.

$$Wreal > Wref \quad (3)$$

If the measured integration value Wreal is greater than the target integration value Wref (step S115—Yes), the controller 11 controls the variable DC power supply 16 and waveform generator 17, thereby decreasing the high-frequency voltage V which is applied by the output of the high-frequency electric power P (step S116). Thereby, when the impedance Z does not vary, the high-frequency current 1 also decreases, and the high-frequency electric power P, which is output from the high-frequency electric power generator 12, also decreases. On the other hand, if the measured integration value Wreal is less than the target integration value Wref (step S115—No), the controller 11 controls the variable DC power supply 16 and waveform generator 17, thereby increasing the high-frequency voltage V which is applied by the output of the high-frequency electric power P (step S117). Thereby, when the impedance Z does not vary, the high-frequency current 1 also increases, and the high-frequency electric power P, which is output from the high-frequency electric power generator 12, also increases.

As illustrated in FIG. 2, before the measured integration value Wreal of the high-frequency electric power P reaches the target stop integration value We which is set by the target locus setting section 35 (step S106—No), the process (step S105) of adjusting the high-frequency voltage V is repeatedly executed with the passage of time. Accordingly, in FIG. 5, during a period between time T1 and time T2, since the absolute value of the difference between the measured integration value Wreal and target integration value Wref is greater than the predetermined threshold $\epsilon th$ and the measured integration value Wreal is less than the target integration value Wref, the controller 11 increases the high-frequency voltage V from a voltage value V1 to a voltage value V2. Thereby, the high-frequency electric power P increases. In addition, during a period between time T2 and time T3, since the absolute value of the difference between the measured integration value Wreal and target integration value Wref is not greater than the predetermined threshold $\epsilon th$, the controller 11 maintains the high-frequency voltage V at the voltage value V2 with the passage of time. Thereby, the magnitude of the high-frequency electric power P is maintained with time. After time T3, since the absolute value of the difference between the measured integration value Wreal and target integration value Wref is greater than the predetermined threshold $\epsilon th$ and the measured integration value Wreal is less than the target integration value Wref, the controller 11 increases the high-frequency voltage V from the voltage value V2 to a voltage value V3. Thereby, the high-frequency electric power P increases.

When the measured integration value Wreal of the high-frequency electric power P reaches the target stop integration value We which is set by the target locus setting section 35 (step S106—Yes), the controller 11 controls the variable DC power supply 16 and waveform generator 17, thereby stopping the output of the high-frequency electric power P from the high-frequency electric power generator 12 (step S107). Thereby, the treatment ends. Specifically, at a time point when the equation (4) is established, the output of the high-frequency electric power P is stopped. In the meantime, an output stop time Te of the high-frequency electric power P is a time point at which the target stop time $\Delta Te$ has passed since the output start time Ts, or a time in the neighborhood of the time point at which the target stop time $\Delta Te$ has passed since the output start time Ts. However, since a small error due to control, etc. exist, the output stop time Te does not necessarily coincide with the time point at which the target stop time $\Delta Te$ has passed since the output start time Ts.

$$Wreal \ge We \quad (4)$$

In the present embodiment, as described above, the target locus, which indicates the time-based variation of the target integration value Wref that is the target value of the integration value W of the high-frequency electric power P, is set. The target locus indicates the time-based variation of the ideal integration value W in the treatment. In addition, in the present embodiment, based on the comparison of the measured integration value Wreal with the target locus, the high-frequency voltage V is adjusted and the output state of the high-frequency electric power P is controlled in such a state that the deviation of the time-based variation of the measured integration value Wreal from the target locus decreases. Thus, in this embodiment, the time ($\Delta Te$) during which the high-frequency electric power P is being output, and the output state, such as the output level, of the high-frequency electric power P (high-frequency voltage V) at each time point when the high-frequency electric power P is output, are adjusted in such a state that proper treatment is performed in the treatment section 6. Specifically, in this embodiment, the high-frequency electric power P is output from the high-frequency electric power generator 12 during a proper output time from the output start time Ts, and the output state, such as the output level, of the high-frequency electric power P is adjusted into an optimal state for treatment, even before the output stop time Te. Accordingly, in the present embodiment, there can be provided the high-frequency control unit 3 in which the output state of the high-frequency electric power P is properly controlled based on the integration value W of the high-frequency electric power P, even before the output stop time Te, and treatment can properly be performed with use of the high-frequency electric power P.

In addition, in the present embodiment, the target stop integration value We and target stop time $\Delta$Te are set based on the impedance Z. Thus, the target stop integration value We and target stop time $\Delta$Te are properly set based on the state of the treated target H, such as the degree of wetting of the treated target H. In addition, the target locus is set based on the properly set target stop integration value We and target stop time $\Delta$Te. Thus, regardless of the state of the treated target H such as the degree of wetting, the target locus, which indicates the time-based variation of the target integration value Wref of the high-frequency electric power P, becomes a locus indicating the ideal time-based variation of the integration value W of high-frequency electric power P in the treatment. Therefore, by controlling the output state of the high-frequency electric power P, based on the comparison of the measured integration value Wreal with the set target locus, the output state of the high-frequency electric power P can properly be controlled in accordance with the state of the treated target H.

Additionally, since the output state of the high-frequency electric power P is controlled based on the comparison result of the measured integration value Wreal with the target locus, the output state of the high-frequency electric power P is adjusted in such a state that the measured integration value Wreal of the high-frequency electric power P becomes substantially equal to the target stop integration value We at a time point at which the target stop time $\Delta$Te has passed since the output start time Ts of the high-frequency electric power P. Thus, at a time point at which the target stop time $\Delta$Te, which was set by the target locus setting section 35, has passed since the output start time Ts, or at a time in the neighborhood of the time point at which the target stop time $\Delta$Te has passed since the output start time Ts, the measured integration value Wreal reaches the target stop integration value We, and the output of the high-frequency electric power P is stopped. Therefore, the time period from the output start time Ts to the output stop time Te, during which the high-frequency electric power P is being supplied, and the integration value W of the high-frequency electric power P from the output start time Ts to the output stop time Te, can be adjusted into a proper state for treatment.

As described above, based on the integration value W of the high-frequency electric power P, the high-frequency voltage V is adjusted, and the output control of the high-frequency electric power P is executed. Thereby, the high-frequency electric power P is always stably supplied to the treatment section 6 from the output start time (supply start time) Ts to the output stop time (supply stop time) Te. Therefore, the treated target H can properly be coagulated and sealed.

Modifications of the First Embodiment

Figure 6:
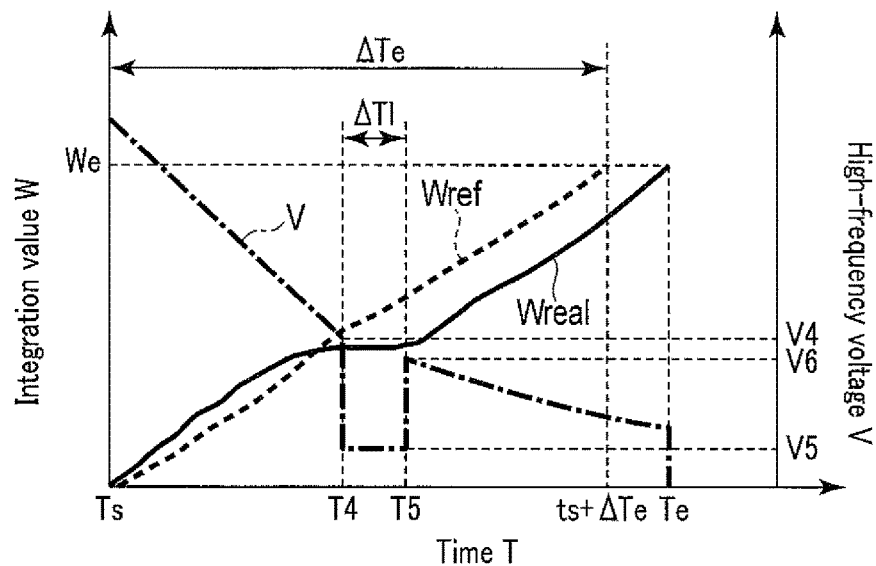
FIG. 6 is a schematic view illustrating an example of time-based variations of a target integration value of high-frequency electric power, a measured integration value of the high-frequency electric power, and a high-frequency voltage in treatment using a high-frequency control unit according to a first modification of the first embodiment.

The aspect of the process (the process illustrated in FIG. 3) of adjusting the high-frequency voltage V and controlling the output of the high-frequency electric power P, on the basis of the comparison result of the measured integration value Wreal with the target locus, is not limited to the first embodiment. For example, in a first modification of the first embodiment, which is illustrated in FIG. 6, the controller 11 controls the output of the high-frequency electric power P, based on the detection result of the impedance Z, when the measured integration value Wreal becomes smaller than the target integration value (reference integration value) Wref and when a measured increase rate $\gamma$real, which is a time-based increase rate of the measured integration value Wreal of the high-frequency electric power P, becomes smaller than a target increase rate (reference increase rate) $\gamma$ref which is a time-based increase rate $\gamma$ of the target integration value Wref on the target locus. In the meantime, FIG. 6 illustrates an example of time-based variations of the target integration value Wref of the high-frequency electric power P, the measured integration value Wreal of the high-frequency electric power P, and the high-frequency voltage V (output level) in the treatment. In addition, in FIG. 6, the abscissa indicates time T, and the ordinate indicates the integration value W of the high-frequency electric power P and the high-frequency voltage V. Further, in FIG. 6, the time-based variation of the measured integration value Wreal is indicated by a solid line, the time-based variation of the target integration value Wref is indicated by a broken line, and the time-based variation of the high-frequency voltage V is indicated by a dash-and-dot line.

In the present modification, when the measured integration value Wreal has become smaller than the target integration value Wref and when the measured increase rate $\gamma$real of the measured integration value Wreal has become smaller than the target increase rate $\gamma$ref of the target integration value Wref, the controller 11 determines whether the impedance Z is greater than a predetermined threshold Zth. When the impedance Z becomes greater than the predetermined threshold Zth, the high-frequency current I, which flows by the output of the high-frequency electric power P, decreases even if the high-frequency voltage V is increased. Thus, even if the high-frequency voltage V (output level) is increased, the high-frequency electric power P, which is output per unit time, decreases, and the measured increase rate $\gamma$real of the measured integration value Wreal of high-frequency electric power P also decreases. Specifically, if the impedance Z increases, it becomes impossible to supply a large high-frequency electric power P to the treated target H, and it becomes impossible to increase the measured increase rate $\gamma$real of the measured integration value Wreal. Accordingly, in the present modification, it is determined whether or not the impedance Z is so large that the high-frequency electric power P, which is supplied, cannot be increased even if the high-frequency voltage V is increased.

Thus, in this modification, when the impedance Z becomes greater than the predetermined threshold Zth, the controller 11 temporarily lowers the high-frequency voltage V (output level). Then, after the high-frequency voltage V in the lowered state is kept for a predetermined reference decrease time $\Delta$Tl, the magnitude (output level) of the high-frequency voltage V is restored to a level before the impedance Z exceeds the predetermined threshold Zth (i.e. before the measured increase rate γreal becomes smaller than the target increase rate γref). In FIG. 6, at time T4, the high-frequency voltage V is lowered from a voltage value V4 to a voltage value V5. Then, during a period between time T4 and time T5, the high-frequency voltage V is kept at the voltage value V5. Then, at time T5, the high-frequency voltage V is increased to a voltage value V6, and the high-frequency voltage V is restored to the original magnitude (output level).

By temporarily decreasing the high-frequency voltage V, the impedance Z of the circuit, in which the high-frequency current I flows, decreases. By the decrease of the impedance Z, the impedance Z lowers to the predetermined threshold Zth or less. Thereby, the high-frequency current I increases, and the high-frequency electric power P also increases. Specifically, by temporarily lowering the high-frequency voltage V (the output level of the high-frequency electric power P), the impedance Z decreases and the supply of the high-frequency electric power P is promoted. By the increase of the high-frequency electric power P, the measured increase rate γreal of the measured integration value Wreal also increases. Accordingly, in the present modification, even in the case in which it becomes impossible to increase the output of the high-frequency electric power P due to the increase of the impedance Z, the impedance Z can be lowered by controlling the output of the high-frequency electric power P as described above. Thereby, the measured increase rate γreal of the measured integration value Wreal increases, and the deviation of the measured integration value Wreal of the high-frequency electric power P from the target locus can be suppressed to a low level. Therefore, in the present modification, too, the high-frequency electric power P is always stably supplied to the treatment section 6 from the output start time Ts to the output stop time Te, and the treated target H can properly be coagulated and sealed.

Furthermore, in the present modification, like the first embodiment, when the measured integration value Wreal reaches the target stop integration value We (i.e. if equation (4) is established), the output of the high-frequency electric power P is stopped. In the example of FIG. 6, the output of the high-frequency electric power P is stopped shortly after a time point (Ts+ΔTe) at which the target stop time ΔTe has passed since the output start time Ts.

Figure 7:
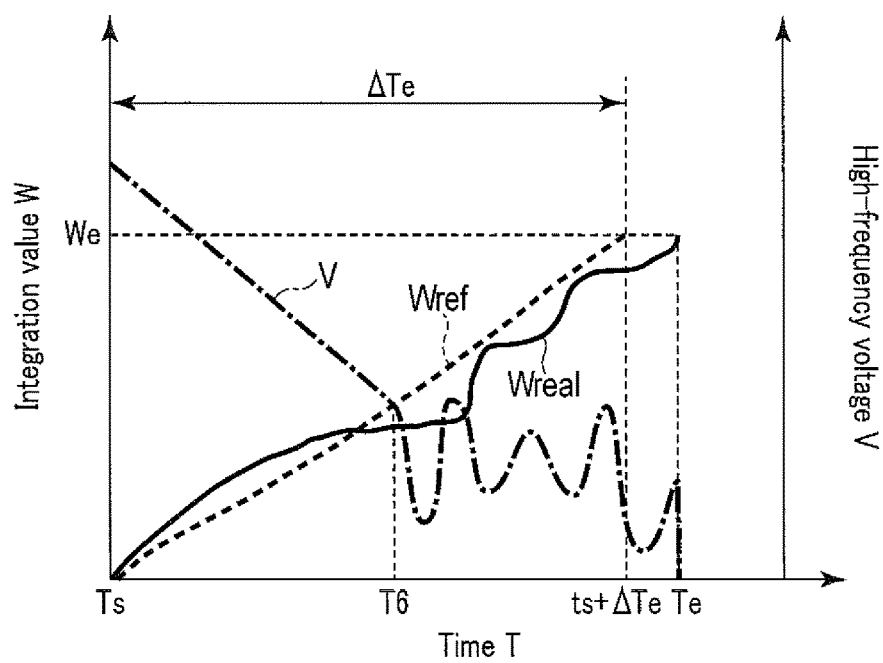
FIG. 7 is a schematic view illustrating an example of time-based variations of a target integration value of high-frequency electric power, a measured integration value of the high-frequency electric power, and a high-frequency voltage in treatment using a high-frequency control unit according to a second modification of the first embodiment.

Also in a second modification of the first embodiment, which is illustrated in FIG. 7, when the measured integration value Wreal becomes smaller than the target integration value Wref and when the measured increase rate γreal, which is the time-based increase rate of the measured integration value Wreal of the high-frequency electric power P, becomes smaller than the target increase rate γref that is the time-based increase rate γ of the target integration value Wref on the target locus, the controller 11 determines whether the impedance Z is greater than the predetermined threshold Zth. In the meantime, FIG. 7 illustrates an example of time-based variations of the target integration value Wref of the high-frequency electric power P, the measured integration value Wreal of the high-frequency electric power 7, and the high-frequency voltage V (output level) in the treatment. In addition, in FIG. 7, the abscissa indicates time T, and the ordinate indicates the integration value W of the high-frequency electric power P and the high-frequency voltage V. Further, in FIG. 7, the time-based variation of the measured integration value Wreal is indicated by a solid line, the time-based variation of the target integration value Wref is indicated by a broken line, and the time-based variation of the high-frequency voltage V is indicated by a dash-and-dot line.

In the present modification, unlike the first modification of the first embodiment, when the impedance Z becomes greater than the predetermined threshold Zth, the controller 11 causes the high-frequency electric power P to be output in a state in which the high-frequency voltage V (output level) is oscillated up and down, compared to a state before the impedance Z exceeds the predetermined threshold Zth (i.e. before the measured increase rate γreal becomes smaller than the target increase rate γref). In the state in which the high-frequency voltage V is oscillated by the controller 11, the voltage value of the high-frequency voltage V oscillates up and down. In FIG. 7, at time T6, switching is effected to the state in which the high-frequency voltage V (output level) is oscillated up and down. Then, from time T6 to the output stop time Te of the high-frequency electric power P, the state in which the high-frequency voltage V is oscillated is maintained.

By oscillating the high-frequency voltage V up and down, the impedance Z of the circuit, in which the high-frequency current I flows, decreases. By the decrease of the impedance Z, the impedance Z lowers to the predetermined threshold Zth or less. Thereby, the high-frequency current I increases, and the high-frequency electric power P also increases. Specifically, by oscillating the high-frequency voltage V (the output level of the high-frequency electric power P) up and down, the impedance Z decreases and the supply of the high-frequency electric power P is promoted. In this modification, too, by the increase of the high-frequency electric power P, the measured increase rate γreal of the measured integration value Wreal also increases. Accordingly, in the present modification, even in the case in which it becomes impossible to increase the output of the high-frequency electric power P due to the increase of the impedance Z, the impedance Z can be lowered by controlling the output of the high-frequency electric power P as described above. Thereby, the measured increase rate γreal of the measured integration value Wreal increases, and the deviation of the measured integration value Wreal of the high-frequency electric power P from the target locus can be suppressed to a low level. Therefore, in the present modification, too, the high-frequency electric power P is always stably supplied to the treatment section 6 from the output start time Ts to the output stop time Te, and the treated target H can properly be coagulated and sealed.

Furthermore, in the present modification, like the first embodiment, when the measured integration value Wreal reaches the target stop integration value We (i.e. if equation (4) is established), the output of the high-frequency electric power P is stopped. In the example of FIG. 7, the output of the high-frequency electric power P is stopped shortly after a time point (Ts+ΔTe) at which the target stop time ΔTe has passed since the output start time Ts.

Besides, in a certain modification of the first embodiment, in step S113 of FIG. 3, the determination based on the absolute value of the difference between the measured integration value Wreal and the target integration value Wref is not executed. Instead, the controller 11 determines whether the measured integration value Wreal agrees with the target integration value Wref. In this case, when the measured integration value Wreal agrees with the target integration value Wref, the high-frequency voltage V (the output level of high-frequency electric power P) is maintained. On the other hand, when the measured integration value Wreal does not agree with the target integration value Wref, the determination of step S115 is executed.

In the above-described first embodiment and modifications thereof, the target locus setting section (35) sets the target stop integration value (We) which is the target integration value (Wref) at the time point at which the output of the high-frequency electric power (P) is stopped, and the target stop time (ΔTe) from the output start time (Ts) until the target integration value (Wref) reaching the target stop integration value (We). Based on the target stop integration value (We) and target stop time (ΔTe), the target locus setting section (35) sets the target locus. In addition, the controller (11) compares, from the output start time (Ts) to the output end time (Te) with the passage of time, the measured integration value (Wreal), which is calculated by the integration value calculator (33), with the target locus which is set by the target locus setting section (35). Then, based on the comparison result, the controller (11), with the passage of time, the output state of the high-frequency electric power (P) from the high-frequency electric power generator (12).

Second Embodiment

Next, a second embodiment of the present invention is described with reference to FIG. 8 and FIG. 9. In the second embodiment, the configuration of the first embodiment is modified as will be described below. Incidentally, the same parts as in the first embodiment are denoted by like reference numerals, and a description thereof is omitted.

In the present embodiment, like the first embodiment, the high-frequency control unit 3 includes the controller 11, high-frequency electric power generator 12, output measuring section 13, etc. In this embodiment, however, the high-frequency electric power generator 12 can output high-frequency electric power P in a first output mode and a second output mode which is different from the first output mode in a control method by the controller 11. In the first output mode and second output mode, since the control method by the controller 11 is different, the output state of the high-frequency electric power P is different, and the high-frequency electric power P, which is output per unit time, is different. Since the high-frequency electric power P, which is output per unit time, is different, the measured increase rate $\gamma real$, which is the time-based increase rate of the measured integration value Wreal of the high-frequency electric power P, is different between the first output mode and second output mode. In the present embodiment, the output of the high-frequency electric power P is controlled in such a state that the measured increase rate $\gamma real$ of the measured integration value Wreal is smaller in the first output mode than in the second output mode.

Figure 8:
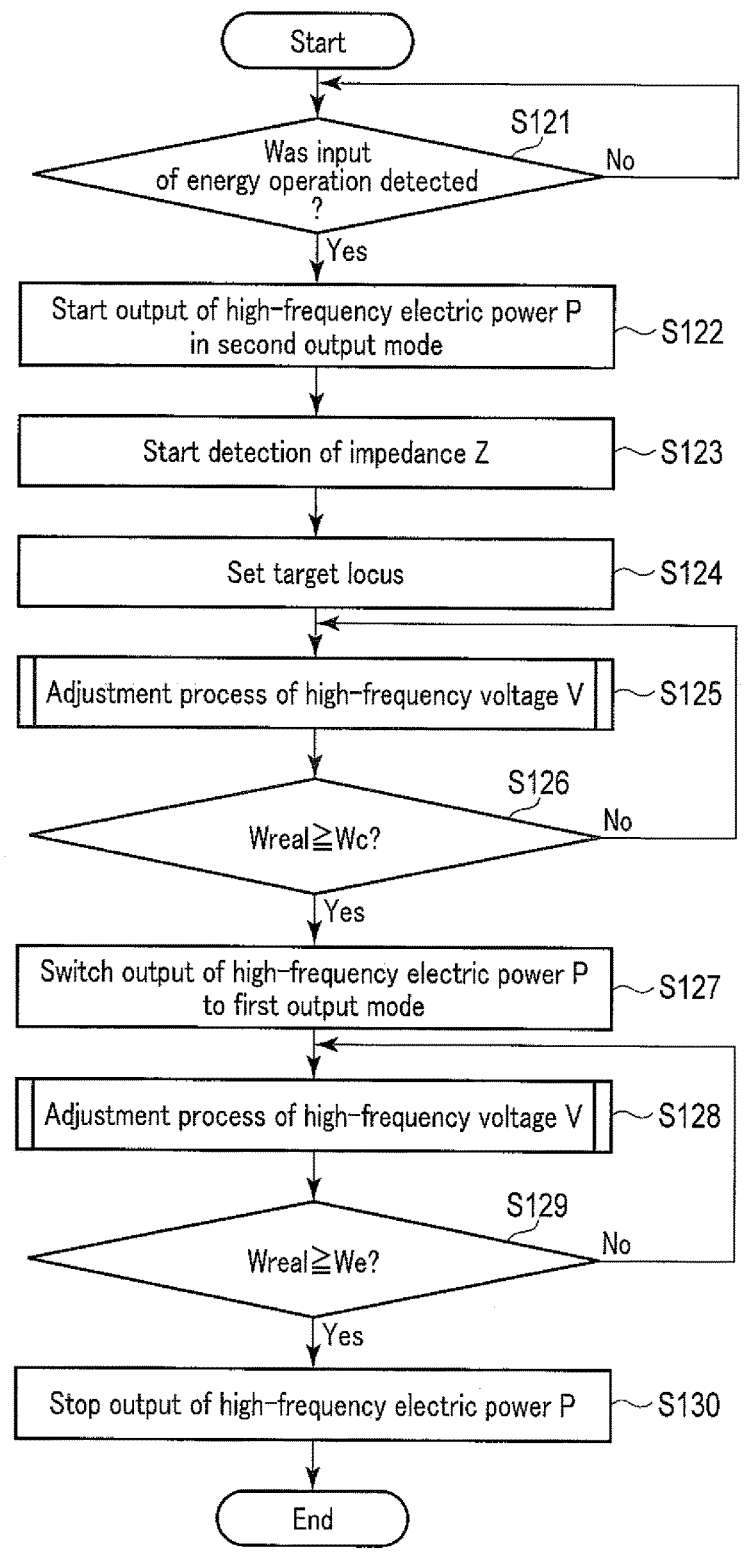
FIG. 8 is a flowchart illustrating a process in treatment by a high-frequency control unit according to a second embodiment.
Figure 9:
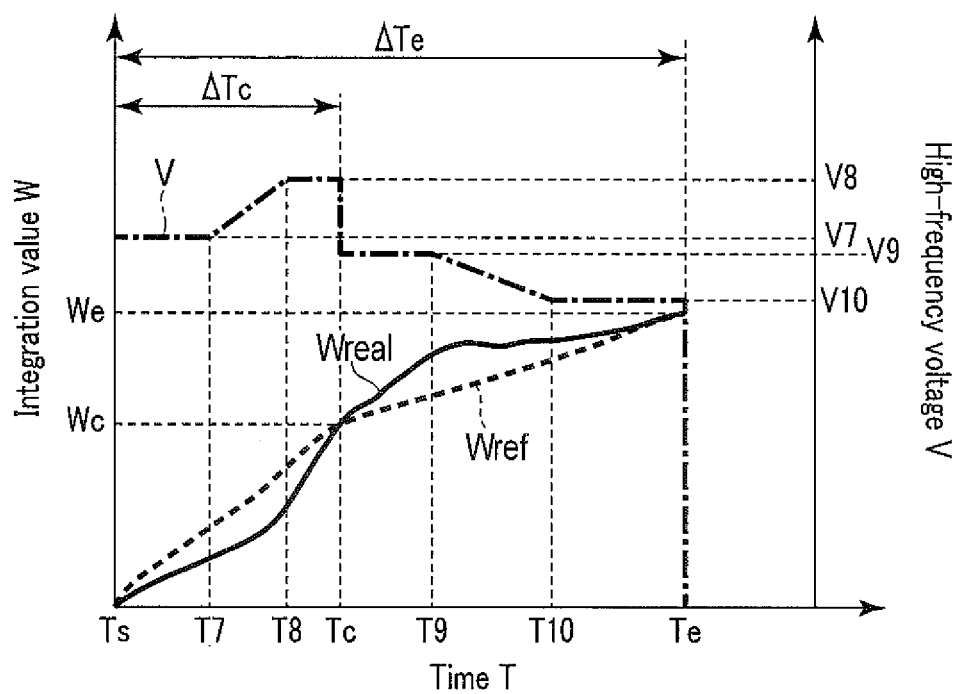
FIG. 9 is a schematic view illustrating an example of time-based variations of a target integration value of high-frequency electric power, a measured integration value of the high-frequency electric power, and a high-frequency voltage in treatment using the high-frequency control unit according to the second embodiment.

FIG. 8 is a flowchart illustrating a process in treatment by the high-frequency control unit 3. FIG. 9 is a graph illustrating an example of time-based variations of the target integration value (reference integration value) Wref of high-frequency electric power P, the measured integration value Wreal of the high-frequency electric power P, and the high-frequency voltage V (output level) in the treatment. In FIG. 9, the abscissa indicates time T, and the ordinate indicates the integration value W of high-frequency electric power P, and the high-frequency voltage V. Further, in FIG. 9, the time-based variation of the measured integration value Wreal is indicated by a solid line, the time-based variation of the target integration value Wref is indicated by a broken line, and the time-based variation of the high-frequency voltage V is indicated by a dash-and-dot line.

As illustrated in FIG. 8, in the present embodiment, when the operation input detector 21 detects an input of an energy operation in the energy operation input section 8 (step S121—Yes), the high-frequency electric power generator 12 (output circuit 18) starts, by the control of the controller 11, an output of high-frequency electric power P in the second output mode (step S122). The high-frequency electric power P is output in the second output mode, mainly while the accretion on the treated target H is being eliminated (i.e. during a period from the output start time Ts until the treatment section 6 coming in contact with the outer surface of the treated target H).

Like the first embodiment, when the output of the high-frequency electric power P is started, the impedance detector 31 starts time-based detection of the impedance Z of the circuit in which the high-frequency current I flows, based on detection results by the current detector 25 and voltage detector 26 (step S123). Then, based on the detection result by the impedance detector 31, the target locus setting section 35 sets a target locus which indicates, with the passage of time, the target integration value Wref which is the target value of the integration value W of the high-frequency electric power P from the output start time Ts (step S124).

In the present embodiment, however, the target locus setting section (reference locus setting section) 35 sets, as the target integration value Wref of high-frequency electric power P, a first target integration value (target stop integration value) We, and a second target integration value (target switch integration value) Wc which is smaller than the first target integration value We. In addition, the target locus setting section 35 sets a first target time (target stop time) ΔTe from the output start time Ts until reaching the first target integration value We, and a second target time (target switch time) ΔTc from the output start time Ts until reaching the second target integration value Wc. Furthermore, the target locus setting section 35 sets a target locus which indicates, with the passage of time, the target integration value Wref of the high-frequency electric power P, on the basis of the set first target integration value (first reference integration value) We, second target integration value (second reference integration value) Wc, first target time (first reference time) ΔTe, and second target time (second reference time) ΔTc. The first target integration value We, second target integration value Wc, first target time ΔTe and second target time ΔTc are set based on the detection result by the impedance detector 31. For example, the target locus setting section 35 sets the first target integration value We, second target integration value Wc, first target time ΔTe and second target time ΔTc, based on at least one of the value Zs of the impedance Z at the output start time Ts of the high-frequency electric power P, the inclination (decrease rate) σ of the variation of the impedance Z from the output start time Ts until the impedance Z reaching the minimum value Zmin, and the time ΔTmin from the output start time Ts until the impedance Z reaching the minimum value Zmin.

The target locus setting section 35 sets the target locus in such a state that the target integration value Wref increases with time at a first target increase rate (first reference increase rate) $\gamma ref1$ from the second target integration value Wc to the first target integration value We. In addition, the target locus setting section 35 sets the target locus in such a state that the target integration value Wref increases with time at a second target increase rate (second reference increase rate) $\gamma ref2$, which is different from the first target increase rate $\gamma ref1$, from the output start time Ts of high-frequency electric power P to the second target integration value Wc. In the present embodiment, the first target increase rate γref1 is smaller than the second target increase rate γref2. Thus, in the target locus of the target integration value Wref illustrated in FIG. 9, the inclination of the locus is smaller during the period from the second target integration value We to the first target integration value We, than during the period from the output start time Ts to the second target integration value Wc.

When the target locus is set, the controller 11 executes a process of adjusting the high-frequency voltage V, based on the target locus (step S125). The process of adjusting the high-frequency voltage V is executed in the same manner as in the first embodiment (i.e. in the manner illustrated in the flowchart of FIG. 3). At this time, the high-frequency electric power P is output in the second output mode in which the measured increase rate γreal of the measured integration value Wreal is high. In the second output mode, since the measured increase rate γreal of the measured integration value Wreal of the high-frequency electric power P (the high-frequency electric power P that is output per unit time) is large, the adhesive material is quickly eliminated. As described above, in the state in which the measured integration value Wreal of the high-frequency electric power P is increasing, with the passage of time, from the output start time Ts to the second target integration value (second reference integration value) Wc, on the basis of the comparison result with the target locus, the controller 11 causes the high-frequency electric power generator 12 to output the high-frequency electric power P in the second output mode. In the meantime, the high-frequency voltage V may be adjusted as described in the modifications of the first embodiment.

As illustrated in FIG. 8, before the measured integration value Wreal of the high-frequency electric power P reaches the second target integration value (target switch integration value) Wc which is set by the target locus setting section 35 (step S126—No), the high-frequency electric power P is output in the second output mode, and the process (step S125) of adjusting the high-frequency voltage V is repeatedly executed with the passage of time. Accordingly, in FIG. 9, during a period between time T7 and time T8, since the absolute value of the difference between the measured integration value Wreal and target integration value Wref is greater than the predetermined threshold εth and the measured integration value Wreal is less than the target integration value Wref, the controller 11 increases the high-frequency voltage V from a voltage value V7 to a voltage value V8. Thereby, the high-frequency electric power P increases. In addition, during a period between time T8 and time (mode switch time) Tc, since the absolute value of the difference between the measured integration value Wreal and target integration value Wref is not greater than the predetermined threshold εth, the controller 11 maintains the high-frequency voltage V at the voltage value V8 with the passage of time. Thereby, the magnitude of the high-frequency electric power P is maintained with time.

When the measured integration value Wreal of the high-frequency electric power P reaches the second target integration value We which is set by the target locus setting unit 35 (step S126—Yes), the controller 11 controls the variable DC power supply 16 and waveform generator 17, thereby switching the output of the high-frequency electric power P from the high-frequency electric power generator 12 from the second output mode to the first output mode (step S127). Specifically, at a time point when equation (5) is established, the output of the high-frequency electric power P is switched to the first output mode. In the meantime, a mode switch time Tc of the high-frequency electric power P is a time point at which the second target time (target switch time) ΔTc has passed since the output start time Ts, or a time in the neighborhood of the time point at which the second target time ΔTc has passed since the output start time Ts. However, since a small error due to control, etc. exist, the mode switch time Tc does not necessarily coincide with the time point at which the second target time ΔTc has passed since the output start time Ts.

$$W\text{real} \geq Wc \quad (5)$$

After the treatment section 6 has come in contact with the outer surface of the treated target H, the high-frequency electric power P is output in the first output mode. In the first output mode, the measured increase rate γreal of the measured integration value Wreal of the high-frequency electric power P (the high-frequency electric power P that is output per unit time) becomes smaller than in the second output mode, and the high-frequency electric power P (high-frequency current I) is properly supplied to the treated target H. In the example illustrated in FIG. 9, the second output mode is switched to the first output mode at the mode switch time Tc, and the controller 11 decreases the high-frequency voltage V (output level) from the voltage value V8 to a voltage value V9. Thereby, in the first output mode, compared to the second output mode, the high-frequency electric power P, which is output per unit time, decreases, and the measured increase rate γreal of the measured integration value Wreal of high-frequency electric power P decreases.

As described above, in the present embodiment, after the output start time Ts, the high-frequency electric power P is output in the second output mode. Thereafter, the high-frequency electric power P is output in the first output mode. In addition, in both the first output mode and second output mode, the output state of the high-frequency electric power P is controlled based on the comparison result of the measured integration value Wreal with the target locus. However, in the second output mode, the controller 11 compares that portion of the target locus, in which the target integration value Wref increases at the second target increase rate γref2, with the measured integration value Wreal. On the other hand, in the first output mode, the controller 11 compares that portion of the target locus, in which the target integration value Wref increases at the first target increase rate γref1, with the measured integration value Wreal. Thus, between the first output mode and second output mode, the control method by the controller 11 is different, and the output state of the high-frequency electric power P is different.

Also after the output state of the high-frequency electric power P was switched to the first output mode, the controller 11 executes the process of adjusting the high-frequency voltage V, based on the target locus (step S128). At this time, too, the process is executed in the same manner as in the first embodiment (i.e. as illustrated in the flowchart of FIG. 3). Accordingly, in the present embodiment, in the state in which the measured integration value Wreal of the high-frequency electric power P is increasing, with the passage of time, from the second target integration value We to the first target integration value We, on the basis of the result of comparison with the target locus, the controller 11 causes the high-frequency electric power generator 12 to output the high-frequency electric power P in the first output mode. In the meantime, the high-frequency voltage V may be adjusted as described in the modifications of the first embodiment.

As illustrated in FIG. 8, before the measured integration value Wreal of the high-frequency electric power P reaches the first target integration value (target stop integration value) We which is set by the target locus setting section 35 (step S129—No), the high-frequency electric power P is output in the first output mode, and the process (step S128) of adjusting the high-frequency voltage V is repeatedly executed with the passage of time. Accordingly, in FIG. 9, during a period between time T9 and time T10, since the absolute value of the difference between the measured integration value Wreal and target integration value Wref is greater than the predetermined threshold $\epsilon$th and the measured integration value Wreal is greater than the target integration value Wref, the controller 11 decreases the high-frequency voltage V from a voltage value V9 to a voltage value V10. Thereby, the high-frequency electric power P decreases. In addition, during a period between time T10 and time (output stop time) Te, since the absolute value of the difference between the measured integration value Wreal and target integration value Wref is not greater than the predetermined threshold $\epsilon$th, the controller 11 maintains the high-frequency voltage V at the voltage value V10 with the passage of time. Thereby, the magnitude of the high-frequency electric power P is maintained with time.

When measured integration value Wreal of the high-frequency electric power P reaches the first target integration value We which is set by the target locus setting section 35 (step S129—Yes), the controller 11 controls the variable DC power supply 16 and waveform generator 17, thereby stopping the output of the high-frequency electric power P from the high-frequency electric power generator 12 (step S130). Specifically, at a time point when the equation (4) is established, the output of the high-frequency electric power P is stopped. In the meantime, an output stop time Te of the high-frequency electric power P is a time point at which the first target time (target stop time) $\Delta$Te has passed since the output start time Ts, or a time in the neighborhood of the time point at which the first target time $\Delta$Te has passed since the output start time Ts. However, since a small error due to control, etc. exist, the output stop time Te does not necessarily coincide with the time point at which the first target time $\Delta$Te has passed since the output start time Ts.

In the present embodiment, like the first embodiment, the target locus, which indicates the time-based variation of the target integration value Wref that is the target value of the integration value W of the high-frequency electric power P, is set. In addition, in the present embodiment, based on the comparison of the measured integration value Wreal with the target locus, the high-frequency voltage V is adjusted and the output state of the high-frequency electric power P is controlled in such a state that the deviation of the time-based variation of the measured integration value Wreal from the target locus decreases. Thus, in this embodiment, the time ($\Delta$Te) during which the high-frequency electric power P is being output, and the output state, such as the output level, of the high-frequency electric power P (high-frequency voltage V) at each time point when the high-frequency electric power P is output, are adjusted in such a state that proper treatment is performed in the treatment section 6. Accordingly, in the present embodiment, too, there can be provided the high-frequency control unit 3 in which the output state of the high-frequency electric power P is properly controlled based on the integration value W of the high-frequency electric power P, even before the output stop time Te, and treatment can properly be performed with use of the high-frequency electric power P.

Additionally, in this embodiment, the target locus setting section 35 sets, as the target integration value of high-frequency electric power P, the first target integration value We and the second target integration value We which is smaller than the first target integration value We. In addition, the target locus is set in such a state that the target integration value Wref increases with time at the first target increase rate $\gamma$ref1 from the second target integration value Wc to the first target integration value We, and that the target integration value Wref increases with time at the second target increase rate $\gamma$ref2, which is different from the first target increase rate $\gamma$ref1, from the output start time Ts to the second target integration value Wc. For example, when an accretion adheres to the treated target H, the output mode of high-frequency electric power P needs to be switched during the period from the output start time Ts to the output stop time Te. In the present embodiment, the target locus is set as described above. Thus, even in the case in which the output mode of high-frequency electric power P needs to be switched during the period from the output start time Is to the output stop time Te, the ideal time-based variation of the integration value W in the treatment can be indicated by the target locus. Thus, by controlling the output state of the high-frequency electric power P on the basis of the comparison result of the measured integration value Wreal of the high-frequency electric power P with the target locus that was set as described above, even in the case in which the output mode of high-frequency electric power P needs to be switched during the period from the output start time Is to the output stop time Te, the output state, such as the output level, of the high-frequency electric power P is adjusted into an optimal state for treatment, and the treatment can be performed with use of the high-frequency electric power P.

Additionally, in this embodiment, the first target integration value (target stop integration value) We, second target integration value (target switch integration value) Wc, first target time (target stop time) $\Delta$Te and second target time (target switch time) $\Delta$Tc are set based on the impedance Z. Thus, the first target integration value We, second target integration value Wc, first target time $\Delta$Te and second target time $\Delta$Tc are properly set based on the state of the treated target H, such as the degree of wetting of the treated target H. In addition, the target locus is set based on the properly set first target integration value We, second target integration value Wc, first target time $\Delta$Te and second target time $\Delta$Tc. Thus, regardless of the state of the treated target H such as the degree of wetting, the target locus, which indicates the time-based variation of the target integration value Wref of the high-frequency electric power P, becomes a locus indicating the ideal time-based variation of the integration value W of high-frequency electric power P in the treatment. Therefore, by controlling the output state of the high-frequency electric power P, based on the comparison of the measured integration value Wreal with the set target locus, the output state of the high-frequency electric power P can properly be controlled in accordance with the state of the treated target H.

Additionally, since the output state of the high-frequency electric power P is controlled based on the comparison result of the measured integration value Wreal with the target locus, the output state of the high-frequency electric power P is adjusted in such a state that the measured integration value Wreal of the high-frequency electric power P becomes substantially equal to the second target integration value (target switch integration value) Wc at a time point at which the second target time (target switch time) $\Delta$Tc has passed since the output start time Ts of the high-frequency electric power P. Thus, at a time point at which the second target time $\Delta$Tc, which was set by the target locus setting section 35, has passed since the output start time Ts, or at a time in the neighborhood of the time point at which the second target time ΔTc has passed since the output start time Ts, the measured integration value Wreal reaches the second target integration value Wc, and the output of the high-frequency electric power P is switched from the second output mode to the first output mode. Therefore, the time period from the output start time Ts to the mode switch time Tc, during which the high-frequency electric power P is being supplied in the second output mode, and the integration value (integration amount) W of the high-frequency electric power P in the second output mode from the output start time Ts to the output switch time Tc, can be adjusted into a proper state for treatment.

Similarly, since the output state of the high-frequency electric power P is controlled based on the comparison result of the measured integration value Wreal with the target locus, the output state of the high-frequency electric power P is adjusted in such a state that the measured integration value Wreal of the high-frequency power P becomes substantially equal to the first target integration value (target stop integration value) We at a time point at which the first target time (target stop time) ΔTe has passed since the output start time Ts of the high-frequency electric power P. Thus, at a time point at which the first target time ΔTe, which was set by the target locus setting section 35, has passed since the output start time Ts, or at a time in the neighborhood of the time point at which the first target time ΔTe has passed since the output start time Ts, the measured integration value Wreal reaches the first target integration value We, and the output of the high-frequency electric power P is stopped. Therefore, the time period from the output start time Ts to the output stop time Te, during which the high-frequency electric power P is being supplied, and the integration value W of the high-frequency electric power P from the output start time Ts to the output stop time Te, can be adjusted into a proper state for treatment.

As described above, in the present embodiment, like the first embodiment, based on the integration value W of the high-frequency electric power P, the high-frequency voltage V is adjusted, and the output control of the high-frequency electric power P is executed. Thereby, the high-frequency electric power P is always stably supplied to the treatment section 6 from the output start time Ts to the output stop time Te. Therefore, the treated target H can properly be coagulated and sealed.

Modifications of the Second Embodiment

In the second embodiment, the output of high-frequency electric power P is switched to the first output mode, based on the reaching of the measured integration value Wreal to the second target integration value Wc. However, the restriction to this is unnecessary. For example, in a first modification of the second embodiment illustrated in FIG. 10, the controller 11 switches the output state of high-frequency electric power P from the high-frequency electric power generator 12 from the second output mode to the first output mode, on the basis of the detection result of the impedance Z by the impedance detector 31.

Figure 10:
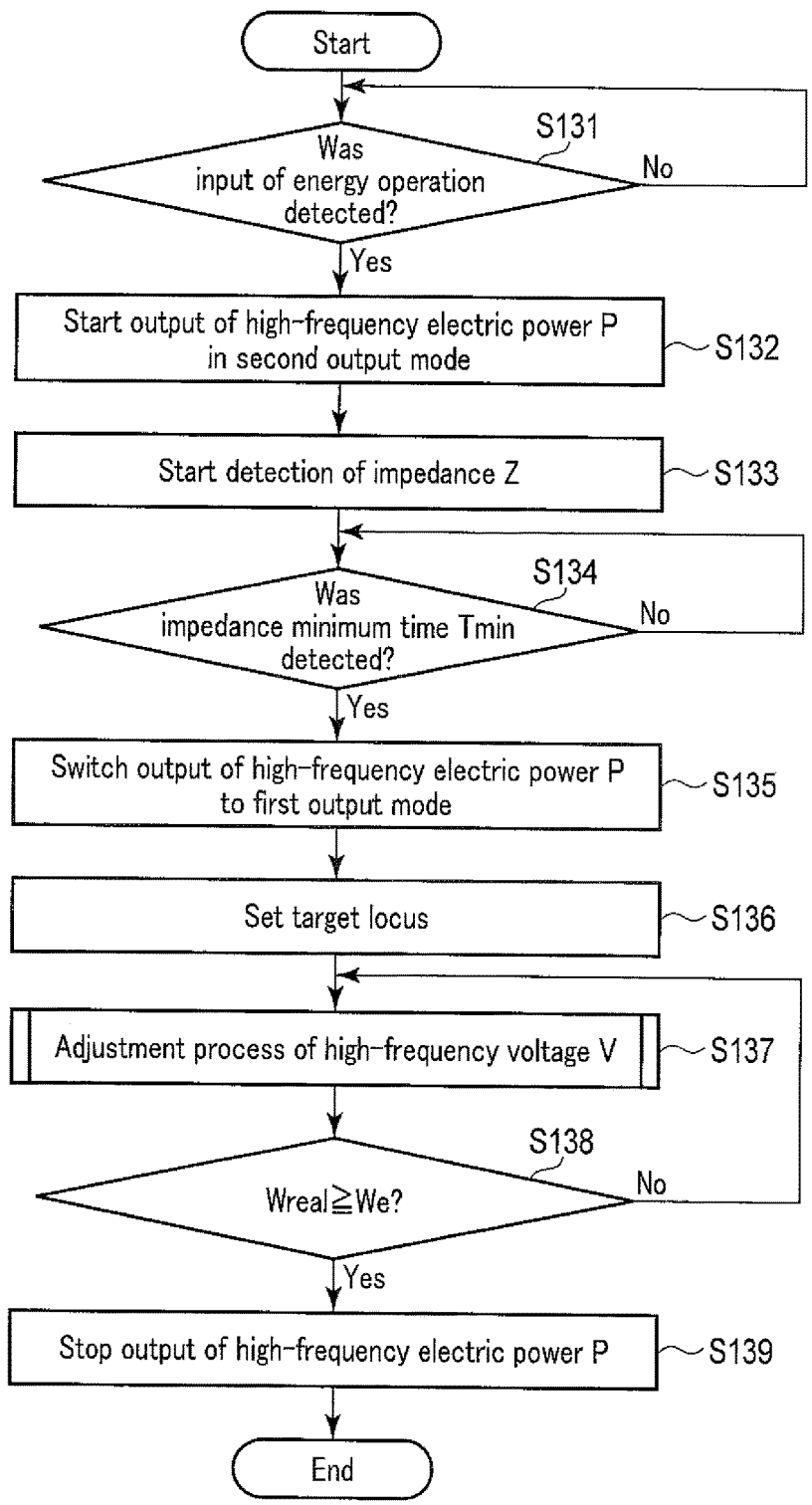
FIG. 10 is a flowchart illustrating a process in treatment by a high-frequency control unit according to a first modification of the second embodiment.

FIG. 10 is a flowchart illustrating a process in treatment by the high-frequency control unit 3. As illustrated in FIG. 10, in the present modification, too, when an input of an energy operation is detected (step S131—Yes), the high-frequency electric power generator 12 starts, by the control of the controller 11, an output of high-frequency electric power P in the second output mode (step S132), and the impedance detector 31 starts detection of the impedance Z (step S133).

In the present modification, after the output start time Ts, when the controller 11 detects an impedance minimum time Tmin (see FIG. 4) at which the impedance Z decreases to a minimum value Zmin (step S134—Yes), the controller 11 switches the output of the high-frequency electric power P from the high-frequency electric power generator 12 from the second output mode to the first output mode (step S135). Specifically, based on the reaching of the impedance Z to the minimum value Zmin, the output state of high-frequency electric power P is switched to the first output mode. As described in the first embodiment, the impedance Z reaches the minimum value (local minimum value) Zmin, at a time point when the treatment section 6 has come in contact with the outer surface of the treated target H, or at a time in the neighborhood of this time point of contact. Thus, the output state of high-frequency electric power P is switched to the first output mode, at a proper timing when the removal of the adhesive material on the treated target H has been completed and the treatment section 6 has begun to come in contact with the outer surface of the treated target H.

When the output state is switched to the first output mode, the target locus setting section 35 sets a target locus which indicates, with the passage of time, the target integration value Wref which is the target value of the integration value W of the high-frequency electric power P from the output start time Ts, on the basis of the detection result by the impedance detector 31 (step S136). In a certain embodiment, like the second embodiment, the target locus setting section 35 sets the first target integration value (target stop integration value) We, second target integration value (target switch integration value) Wc, first target time (target stop time) ΔTe from the output start time Is until reaching the first target integration value We, and second target time (target switch time) ΔTc from the output start time Is until reaching the second target integration value Wc. Furthermore, the target locus setting section 35 sets a target locus which indicates, with the passage of time, the target integration value Wref of the high-frequency electric power P, on the basis of the set first target integration value We, second target integration value Wc, first target time ΔTe, and second target time ΔTc. At this time, it is not necessary to set the target locus from the output start time Ts until the target integration value Wref reaching the first target integration value We. It should suffice if the target locus is set at least between the second target integration value Wc and the first target integration value We.

Besides, in another example, the target locus setting section 35 sets the target stop integration value We which is the first target integration value at which the output of high-frequency electric power P is stopped, and the target stop time ΔTe which is the first target time from the output start time Ts until reaching the target stop integration value We. In addition, from the integration value calculator 33, the measured integration value Wreal of high-frequency electric power P at the time point Tc of the switching to the first output mode (the time point at which the impedance Z has decreased to the minimum value Zmin) is acquired as a switch time integration value (second target integration value) Wc. Then, a target locus, which increases with time from the switch time integration value Wc to the target stop integration value We, is set.

When the target locus is set, like the second embodiment, the controller 11 executes a process of adjusting the high-frequency voltage V, based on the target locus (step S137). In this case, the process is executed in the same manner as in the first embodiment and second embodiment (i.e. in the manner illustrated in the flowchart of FIG. 3). At this time, the high-frequency electric power P is being output in the first output mode. Accordingly, in the present modification, in the state in which the measured integration value Wreal of high-frequency electric power P is increasing, with the passage of time, from the second target integration value (switch time integration value) Wc to the first target integration value (target stop integration value), on the basis of the result of comparison with the target locus, the controller 11 causes the high-frequency electric power generator 12 to output the high-frequency electric power P in the first output mode. Specifically, in the first output mode, the controller 11 controls the output state of the high-frequency electric power P, based on the comparison result of the measured integration value Wreal with the target locus. In the meantime, the high-frequency voltage V may be adjusted as described in the modifications of the first embodiment.

When the measured integration value Wreal of high-frequency electric power P reaches the first target integration value Wc which is set by the target locus setting section 35 (step S138—Yes), the controller 11, like the second embodiment, controls the variable DC power supply 16 and waveform generator 17, thereby stopping the output of the high-frequency electric power P from the high-frequency electric power generator 12 (step S139).

In the above-described second embodiment and modifications thereof, the high-frequency electric power generator (12) can output high-frequency electric power (P) in the first output mode and the second output mode which is different from the first output mode in the control method by the controller (11). After the output start time (Ts), the high-frequency electric power generator (12) outputs the high-frequency electric power (P) in the second output mode, and thereafter outputs the high-frequency electric power (P) in the first output mode. Then, at least in the first output mode, the controller (11) controls the output state of the high-frequency electric power (P), based on the comparison result of the measured integration value (Wreal) with the target locus.

Other Modifications

In the meantime, in the above-described embodiments, only the high-frequency electric power P is supplied to the treatment section 6. However, in addition to the high-frequency electric power P, other treatment energy, such as energy of an ultrasonic transducer, heat, etc., may be supplied to the treatment section 6.

In the above-described embodiments including the first embodiment and second embodiment, a high-frequency control unit (3) includes a high-frequency electric power generator (12) configured to generate high-frequency electric power (P) which is supplied to a treatment section (6); an electric power detector (32) configured to detect, with a passage of time, the high-frequency electric power (P) which is output from the high-frequency electric power generator (12); and an integration value calculator (33) configured to calculate, based on a detection result by the electric power detector (32), a measured integration value (Wreal) with a passage of time, the measured integration value being a measured value of an integration value of the output high-frequency electric power (P) from an output start time (Ts). In addition, the high-frequency control unit (3) includes a target locus setting section (35) configured to set a target locus which indicates, with a passage of time, a target integration value (Wref) which is a target value of the integration value of the output high-frequency electric power (P) from the output start time (Ts); and a controller (11) configured to compare, with a passage of time, the measured integration value (Wreal), which is calculated by the integration value calculator (33), with the target locus set by the target locus setting section (35), and to control, based on a comparison result, an output state of the high-frequency electric power (P) from the high-frequency electric power generator (12) with a passage of time.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A high-frequency control unit for use in a high-frequency treatment system, comprising:
a high-frequency electric power generator configured to generate high-frequency electric power which is supplied to a treatment section;
an electric power detector configured to detect, with a passage of time, the high-frequency electric power which is output from the high-frequency electric power generator;
an integration value calculator configured to calculate, based on a detection result by the electric power detector, a measured integration value with a passage of time, the measured integration value being a measured value of an integration value of the output high-frequency electric power from an output start time;
a target locus setting section configured to:
set a target locus which indicates, with a passage of time, a target integration value that is a target value of the integration value of the output high-frequency electric power from the output start time, the target locus indicating a relationship between the target value of the integration value of the output high frequency electric power and a passed time from the output start time;
set as the target integration value of the high-frequency electric power, a first target integration value and a second target integration value, which is smaller than the first target integration value;
set the target locus in such a state that the target integration value increases with time at a first target increase rate from the second target integration value to the first target integration value; and
set the target locus in such a state that the target integration value increases with time at a second target increase rate, which is different from the first target increase rate, from the output start time of the high-frequency electric power to the second target integration value;
a controller configured to:
compare, with a passage of time, the measured integration value, which is calculated by the integration value calculator, with the target locus set by the target locus setting section; and
control, with a passage of time, an output state of the high-frequency electric power from the high-frequency electric power generator based on a result of the comparison of the measured integration value with the target locus; and
an impedance detector configured to detect, with a passage of time, an impedance of a circuit in which a high-frequency current flows by the output of the high-frequency electric power; wherein:

the high-frequency electric power generator is also configured to:

output the high-frequency electric power in a first output mode and a second output mode, which is different from the first output mode, in a control method performed by the controller; and output, after the output start time, the high-frequency electric power in the second output mode, and configured to thereafter output the high-frequency electric power in the first output mode;

the controller is also configured to:

control, at least in the first output mode, the output state of the high-frequency electric power based on the comparison result of the measured integration value with the target locus;

cause the high-frequency electric power generator to output the high-frequency electric power in the first output mode in a state in which the measured integration value of the high-frequency electric power is increasing, with a passage of time, from the second target integration value to the first target integration value based on the comparison result with the target locus;

stop the output of the high-frequency electric power from the high-frequency electric power generator upon the measured integration value of the high-frequency electric power reaching the first target integration value;

control the output state of the high-frequency electric power, based on the comparison result of the measured integration value with the target locus, in the second output mode in addition to the first output mode;

cause the high-frequency electric power generator to output the high-frequency electric power in the second output mode in a state in which the measured integration value of the high-frequency electric power is increasing, with a passage of time, from the output start time to the second target integration value based on the comparison result with the target locus; and switch the output state of the high-frequency electric power from the high-frequency electric power generator from the second output mode to the first output mode upon the measured integration value of the high-frequency electric power reaching the second target integration value; and the target locus setting section is further configured to set, based on a detection result by the impedance detector, the first target integration value, the second target integration value, a first target time from the output start time until the target integration value reaches the first target integration value, and a second target time from the output start time until the target integration value reaches the second target integration value.

2. The high-frequency control unit of claim 1, wherein the target locus setting section is further configured to set the first target integration value, the second target integration value, the first target time, and the second target time based on at least one of a value of the detected impedance at the output start time of the high-frequency electric power, an inclination of a variation of the detected impedance from the output start time until the detected impedance reaches a minimum value, and a time from the output start time until the detected impedance reaches the minimum value.

3. A high-frequency control unit for use in a high-frequency treatment system, comprising:

a high-frequency electric power generator configured to generate high-frequency electric power which is supplied to a treatment section;

an electric power detector configured to detect, with a passage of time, the high-frequency electric power which is output from the high-frequency electric power generator;

an integration value calculator configured to calculate, based on a detection result by the electric power detector, a measured integration value with a passage of time, the measured integration value being a measured value of an integration value of the output high-frequency electric power from an output start time;

a target locus setting section configured to set a target locus which indicates, with a passage of time, a target integration value that is a target value of the integration value of the output high-frequency electric power from the output start time, the target locus indicating a relationship between the target value of the integration value of the output high frequency electric power and a passed time from the output start time;

a controller configured to:

compare, with a passage of time, the measured integration value, which is calculated by the integration value calculator, with the target locus set by the target locus setting section; and control, with a passage of time, an output state of the high-frequency electric power from the high-frequency electric power generator based on a result of the comparison of the measured integration value with the target locus; and an impedance detector configured to detect, with a passage of time, an impedance of a circuit in which a high-frequency current flows by the output of the high-frequency electric power; wherein:

the high-frequency electric power generator is also configured to:

output the high-frequency electric power in a first output mode and a second output mode, which is different from the first output mode, in a control method performed by the controller; and output, after the output start time, the high-frequency electric power in the second output mode, and configured to thereafter output the high-frequency electric power in the first output mode; and the controller is also configured to:

control, at least in the first output mode, the output state of the high-frequency electric power based on the comparison result of the measured integration value with the target locus;

cause the high-frequency electric power generator to output the high-frequency electric power in the second output mode at the output start time; and configured to switch, after the output start time, the output state of the high-frequency electric power from the high-frequency electric power generator from the second output mode to the first output mode based on a detection result by the impedance detector.

4. The high-frequency control unit of claim 3, wherein the controller is further configured to switch, after the output start time, the output state of the high-frequency electric power from the high-frequency electric power generator from the second output mode to the first output mode based on the detected impedance reaching a minimum value.

5. A high-frequency control unit for use in a high-frequency treatment system, comprising:
- a high-frequency electric power generator configured to generate high-frequency electric power which is supplied to a treatment section;
- an electric power detector configured to detect, with a passage of time, the high-frequency electric power which is output from the high-frequency electric power generator;
- an integration value calculator configured to calculate, based on a detection result by the electric power detector, a measured integration value with a passage of time, the measured integration value being a measured value of an integration value of the output high-frequency electric power from an output start time;
- a target locus setting section configured to set:
  - a target locus which indicates, with a passage of time, a target integration value that is a target value of the integration value of the output high-frequency electric power from the output start time, the target locus indicating a relationship between the target value of the integration value of the output high frequency electric power and a passed time from the output start time;
  - a target stop integration value, which is the target integration value at a point in time at which the output of the high-frequency electric power is stopped;
  - a target stop time from the output start time until the target integration value reaches the target stop integration value; and
  - the target locus based on the target stop integration value and the target stop time;
- a controller configured to:
  - compare, with a passage of time, the measured integration value, which is calculated by the integration value calculator, with the target locus set by the target locus setting section; and
  - control, with a passage of time, an output state of the high-frequency electric power from the high-frequency electric power generator based on a result of the comparison of the measured integration value with the target locus; and
- an impedance detector configured to detect, with a passage of time, an impedance of a circuit in which a high-frequency current flows by the output of the high-frequency electric power; wherein:
- the high-frequency electric power generator is also configured to:
  - output the high-frequency electric power in a first output mode and a second output mode, which is different from the first output mode, in a control method performed by the controller; and
  - output, after the output start time, the high-frequency electric power in the second output mode, and configured to thereafter output the high-frequency electric power in the first output mode; and
- the controller is also configured to control, at least in the first output mode, the output state of the high-frequency electric power based on the comparison result of the measured integration value with the target locus; and
- the target locus setting section is also configured to set the target stop integration value and the target stop time based on a detection result by the impedance detector.

6. The high-frequency control unit of claim 5, wherein the target locus setting section is further configured to set the target stop integration value and the target stop time based on at least one of a value of the detected impedance at the output start time of the high-frequency electric power, an inclination of a variation of the detected impedance from the output start time until the detected impedance reaches a minimum value, and a time from the output start time until the detected impedance reaches the minimum value.

* * * * *